United States Patent [19]

Corden

[11] 4,315,942
[45] Feb. 16, 1982

[54] INTRAVENOUSLY ADMINISTRABLE IRON SUPPLEMENT

[75] Inventor: Brian J. Corden, Kensington, Md.

[73] Assignee: New England Medical Center, Inc., Boston, Mass.

[21] Appl. No.: 40,899

[22] Filed: May 21, 1979

[51] Int. Cl.$^3$ ................. A61K 31/295; C07F 15/02
[52] U.S. Cl. ............................ 424/295; 260/439 R
[58] Field of Search .................. 424/295; 260/439 R

[56] References Cited

U.S. PATENT DOCUMENTS 3,629,446 12/1971 Frohberger et al. ............. 424/289

OTHER PUBLICATIONS

*Husa's Pharmaceutical Dispensing*, Martin Sixth Ed., Mack Pub. Co., Easton Penna, 1966, pp. 400 & 401.
*Helv., Chim. Acta*, 46 1390 (1963); 46 1400 (1963).
Package Insert from Freamine®, McGaw Laboratories.
*Bioinorganic Chemistry*, 9, 255-275 (1978).

*Primary Examiner*—Frederick E. Waddell
*Attorney, Agent, or Firm*—Millen & White

[57] ABSTRACT

The iron (III) complexes of the formula $$Fe(RCONHOH)_3$$

wherein R is H or lower alkyl, are excellent iron supplements which are even intravenously administrable.

12 Claims, No Drawings

INTRAVENOUSLY ADMINISTRABLE IRON SUPPLEMENT

BACKGROUND OF THE INVENTION

The present invention relates to a new form of bioavailable iron which is even safely intravenously administrable Iron deficient anemia is ubiquitous. It is one of the truly universal afflictions. Since the late 19th century iron preparations have been available, and oral ferrous sulfate is still a safe, cheap and effective means of replenishing iron stores in the vast majority of anemic patients. However, it does have considerable disadvantages associated with its use, e.g., side effects of nausea, vomiting, constipation, etc. These are due, at least in part, to the relatively large daily doses required for adequate absorption and hemoglobin response.

Moreover, ferrous sulfate cannot be administered intravenously. In fact, there is presently no satisfactory, intravenously administrable iron supplement. Yet, in certain cases it is impossible to give oral iron preparations. For example, patients who can take nothing by mouth and receive total parenteral nutrition (TPN) frequently require transfusion therapy merely to replenish diminished iron. Premature and sick infants often require extended periods of TPN which exacerbates the normal physiologic anemia of the newborn. TPN is conventionally effected by intravenous administration of commercially available TPN solutions. Although containing most essential vitamins, minerals and amino acids, currently available TPN solutions do not contain iron since there is no acceptable intravenous form.

Other situations also exist in which one must forego the oral route of iron administration. These involve certain patients with iron deficient anemia associated with pregnancy or chronic renal failure and patients unable to take oral iron for any reason.

Such patients often receive painful intramuscular (IM) injections of an iron dextran complex to satisfy their iron supplement requirements. (See, e.g., U.S. Pat. No. Re. 27,240.) All the patients mentioned above would greatly benefit from a safe form of intravenous (IV) iron.

Various forms of iron have been suggested for intravenous administration, e.g., Fe bound to polymeric substrates, or chelated by various ligands, saccharates, dextrans, etc. (See, e.g., U.S. Pat. Nos. 3,886,267, 3,367,834, 4,058,621, 3,275,514 and 3,686,397.) However, all have been unsuccessful and/or possess such adverse side effects that practical utilization has not occurred. The only commercially available intravenous iron preparation is iron dextran (Imferon $^R$). However, IV administration of this compound is accompanied by an unacceptable incidence of anaphylaxis, which has severely limited its use (Physicians' Desk Reference, p. 1201 (1979)).

SUMMARY OF THE INVENTION

Accordingly, it is an object of this invention to provide a form of bioavailable iron which is safely, conveniently and effectively administrable especially intravenously and also orally and/or intramuscularly with minimal side effects.

Upon further study of the specification and appended claims, further objects and advantages of this invention will become apparent to those skilled in the art.

These objects have been achieved by providing a method of increasing the amount of bioavailable iron in a mammal, including humans, which comprises administering to the mammal an amount of the iron (III) complex of an hydroxamic acid of the formula RCONHOH wherein R is H or lower alkyl, especially lower alkyl, effective to increase the amount of bioavailable iron. The iron (III) complex of acetohydroxamic acid is preferred. The complexes per se wherein R is H or $C_{2-6}$ alkyl form another aspect of this invention.

There is also provided a pharmaceutical composition for increasing the amount of bioavailable iron which comprises an amount of the iron (III) complex of an acid as defined above, preferably in a sterilized environment for IV administration, effective to increase the amount of bioavailable iron, and a pharmaceutically acceptable carrier, also preferably sterilized for IV administration. This composition is preferably handled under sterile conditions and stored in a sterile container such as an ampoule for IV administration.

DETAILED DISCUSSION

The iron complexes of this invention have the formula

$$Fe(RCONHON)_3$$

wherein R as lower alkyl contains, e.g., 1–6 carbon atoms. They are readily prepared by direct reaction of the desired hydroxamic acid (RCONHOH) and a water soluble ferric salt such as ferric chloride, ferric perchlorate, etc. in aqueous solution. The reaction is normally conducted at room temperature, e.g. at a pH of 6–8, e.g., using a phosphate, bicarbonate, etc. buffer. Normally, conventional excess amounts (1–1.5 equivalents) of the acid ligand are employed. Of course, any other conventional, and preferably physiologically, acceptable iron salt and/or buffer can be employed.

Preferably, relatively pure types of water, e.g., deionized, doubly distilled, etc. are employed for the reaction in view of the preferred subsequent sterilization of the complex and its environment.

The iron (III) complex per se of acetohydroxamic acid is known (Schwarzenbach et al, Helv., Chim. Acta 46, 1390 (1963); Anderegg et al, Helv. Chim. Acta 46, 1400 (1963)).

The complexes may be administered orally or parenterally, the latter, especially intravenously, being the most advantageous route at least in view of the present state of the art. Generally, details of administration can be determined by procedures analogous to those employed to determine the modes of administration for conventional iron supplements, e.g., orally as with ferrous sulfate, or intravenously and intramuscularly as with the iron dextran complexes, e.g., Imferron $^R$, in each case unless indicated otherwise herein.

For example, suitable dosages by any method of administration may be conventionally determined in accordance with routine experiments, clinical tests, and/or conventional procedures in consideration of the iron levels desired to be achieved, e.g., in treating iron deficiency anemia. Generally, oral dosages of about 100–1000 mg (i.e., as in conventional, 1–10 mg/kg/day based on Fe); IV dosages of about 1–50 mg/kg/day; and IM dosages of about 100–600 mg/kg/day are suitable. These dosages are intended to be non-limiting since, in all cases, higher or lower amounts may be administered when appropriate, the selected dosage being chosen by conventional considerations.

Suitable unit dosages include 50-500 mg orally; 1-5 mg IV; and 5-200 mg IM. However, greater or lesser unit dosages will be employed where suitable.

The particular dose for each specific patient depends on diverse factors as usual, for example, on the age, the body weight, the general state of health, sex, and the diet of the patient; on the time and route of administration; on the rate of excretion; on the combination of medications being taken by the patient; and on the severity of the particular disorder for which therapy is being given, e.g., the hemoglobin level of the patient, etc.

The pharmaceutical compositions of this invention may be formulated into suitable dosage forms for any mode of administration using conventional considerations of galenic pharmacy.

Excipients which can be used are primarily water, preferably sterilized. Other solvents compatible with the complex may also be employed. Formulations used for enteral administration are, in particular, syrups, elixers, tonics, drops or suppositories; for parenteral administration are solutions, preferably aqueous solutions, and also suspensions, emulsions or implants. The indicated formulations can be sterilized and/or contain compatible auxiliaries, such as lubricants, preservatives, stabilizing agents and/or wetting agents, emulsifiers, salts for influencing the osmotic pressure, buffer substances, dyestuffs, flavorings and/or aroma generating substances. They can, if desired, also contain one or more additional active ingredients, for example, one or more vitamins, minerals, amino acids, etc.

The pH of the pharmaceutical solutions of the complex is 6-8, preferably around 7 in view of the stability of the complex.

Particularly preferred compositions are the intravenous preparations. As such, they, of course, consist of sterilized solutions (e.g., in water) and are stored in sterilized containers such as ampoules, infusion bottles, etc. An especially useful dosage form is a conventional TPN solution (e.g., FreAmine$^R$ II by McGaw Laboratories (e.g., Package Insert for FreAmine $^R$ II, McGaw Laboratories, Irvine, Calif. May, 1977 Pamphlet No. Y 36-692); Veinamine $^R$ by Cutter Laboratories; Amino-syn $^R$ by Abbot Laboratories), containing the desired dosage of an iron complex of this invention. Similarly, other conventional IV preparations may be adapted for use in iron therapy by inclusion of an iron complex of this invention therein, e.g., IV preparations for dialysis, saline solutions, dextrose (e.g., 5%), sterilized water, etc.

In solution form, the iron complex preparations generally contain a carrier of water (preferably sterilized), the complex and, optionally, a buffer to maintain the preferred pH of 6-8. The concentration of the iron (III) complex in a dosage unit, the overall size of a dosage unit (ampoule volume, tablet weight, IV bottle volume, etc.) can be selected in accordance with fully conventional considerations.

The iron complexes of this invention can be used for any indications in mammals, including humans, requiring an iron supplement, especially in treating iron deficiency anemia. They are thus useful as a hematinic. They are also useful, e.g., intravenously, as a source of bioavailable iron for humans unable to absorb iron orally. They provide a relatively inexpensive source of iron without bothersome side effects such as gastrointestinal disturbances, anaphylaxis, pain from injection, etc. Moreover, the by-products are excreted rapidly via the urine and the complexes are well tolerated, e.g., have low toxicity.

The terms "sterile" and "sterilized" as used herein have their conventional meanings as understood by skilled artisans when referring to the sterility required pharmaceutically for intravenous preparations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of an iron (III) complex

A solution of the iron (III) complex of acetohydroxamic acid was prepared in the following manner; 100 mg of acetohydroxamic acid

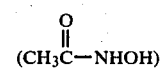

was dissolved in 20-30 ml of deionized water. This was added to 30 mg of anhydrous ferric chloride. The resulting solution was made close to the mark in a 100 ml volumetric flask. 4 ml of a 0.25 M phosphate buffer (pH=7.4) was then added and the resulting solution diluted right up to the 100 ml mark with deionized water. This stock solution was deep orange in color and stable for several days after which crystals (probably iron phosphates) were observed. The stock solution was:

$2.47 \times 10^{-3}$ M in FeCl$_3$
$1.33 \times 10^{-2}$ M in acetohydroxamic acid (HA)
0.010 M in phosphate buffer (pH=7.4)
giving: $2.47 \times 10^{-3}$ M Fe(III) (HA)$_3$
with: $5.8 \times 10^{-3}$ M excess HA

EXAMPLE 2

Efficacy of the complex to increase bioavailable iron

A 17 kg dog was premedicated and then anesthesized with IV sodium amytal. Through a femoral vein cutdown, the following studies were drawn before and after the addition of the iron complex solution: Hgb, Hct, serum Fe and TIBC (Total Iron Binding Capacity). In addition, serum Fe and TIBC were drawn after the addition of one half of the solution.

40 ml of fresh stock solution (containing 6 mg of iron) were given by IV push through the femoral vein. The dog's ECG was monitored throughout the procedure. In approximately 10 minutes, the second set of studies were drawn and a second 40 ml were pushed. The final set of blood studies were drawn in approximately 10 minutes. At no time did the ECG demonstrate arrhythmias. The results are summarized in the table below:

| Test performed on dog** | Before injection of complex | After injection of 6 mg Fe | After injection of 12 mg Fe |
|---|---|---|---|
| Hgb (g%) | 6.7 | — | 6.5 |

-continued

| Test performed on dog** | Before injection of complex | After injection of 6 mg Fe | After injection of 12 mg Fe |
| --- | --- | --- | --- |
| Hct (%) | 20.5 | — | 20.0 |
| serum Fe (μg/100 ml) | 235* | 360 | 470 |
| TIBC (μg/100 ml) | 360 | 360 | 330 |

*This value is high in the face of a low Hbg value, probably because the dog had been fed an iron rich diet.
**Total Blood Volume: 1.36 l
Plasma Volume: 1.09 l
Body TIBC: 3.92 mg
Unsaturated Iron Binding Capacity (UIBC): 1.37 mg
% Saturation of Transferrin: 65%

As the data shows, addition of 6 mg of iron in the form of the ferric acetohydroxamic acid complex saturated the serum transferrin (serum Fe went from 235μg/100 ml to 360μg/100 ml, a value equal to the TIBC). Addition of a further 6 mg gave a serum iron of *greater* than the TIBC. These results show that ferric acetohydroxamic acid complex can be safely administered intravenously and is capable of saturating serum transferrin in vivo.

EXAMPLE 3

Preparation of an ampoule

A solution of about 2.5 m M iron (III) complex of acetohydroxamic acid in twice distilled water is sterile-filtered and filled into ampoules, which are sealed under sterile conditions. Each ampoule contains 25 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of increasing the amount of bioavailable iron in a mammal which comprises administering to the mammal an amount of an iron (III) complex of the formula $Fe(RCHNOH)_3$ wherein R is H or $C_{2-6}$ alkyl or of the iron (III) complex of acetohydroxamic acid effective to increase the amount of bioavailable iron.

2. The method of claim 1, wherein the iron (III) complex consists essentially of that of acetohydroxamic acid.

3. The method of claim 2, wherein the administering is intravenously.

4. The method of claim 2, wherein the administering is orally.

5. The method of claim 2, wherein the mammal is suffering from iron deficiency anemia.

6. A pharmaceutical composition for increasing the amount of bioavailable iron in a mammal which comprises an amount of an iron (III) complex of claim 1 or of the iron (III) complex of acetohydroxamic acid effective to increase the amount of bioavailable iron and a pharmaceutically acceptable carrier, with the proviso that when the carrier is water (a) the solution is sterile; (b) the solution is isotonic; or (c) the solution has a pH of 6–8.

7. The pharmaceutical composition of claim 6, wherein the iron (III) complex consists essentially of that of acetohydroxamic acid.

8. The composition of claim 7, which is an injection solution.

9. The composition of claim 6, which is a total parenteral nutrition solution.

10. The composition of claim 7, which is an isotonic aqueous solution.

11. The composition of claim 7, which is an aqueous solution having a pH of 6–8.

12. The composition of claim 7, which is sterile and has a pH of 6–8.

* * * * *